US00PP30280P2

(12) United States Plant Patent
Hansen

(10) Patent No.: US PP30,280 P2
(45) Date of Patent: Mar. 5, 2019

(54) ***AGAVE* PLANT NAMED 'STINGRAY'**

(50) Latin Name: ***Agave bracteosa* (Zucc.)**
Varietal Denomination: Stingray

(71) Applicant: Hans A Hansen, Zeeland, MI (US)

(72) Inventor: Hans A Hansen, Zeeland, MI (US)

( * ) Notice: Subject to any disclaimer, the term of this patent is extended or adjusted under 35 U.S.C. 154(b) by 0 days.

(21) Appl. No.: 15/932,168

(22) Filed: Feb. 14, 2018

(51) Int. Cl.
*A01H 5/00* (2018.01)

(52) U.S. Cl.
USPC ..... Plt./373

(58) Field of Classification Search
USPC ..... Plt./373
See application file for complete search history.

*Primary Examiner* — Annette H Para

(57) ABSTRACT

A new and unique *Agave* plant named 'Stingray' characterized by upright plant habit near base and arching to drooping distally. Leaves are long, narrow and attractively variegated leaves with creamy yellow margins and medium green centers. The plant is useful in the landscape as a specimen, en masse, or also in a container in the home or landscape.

1 Drawing Sheet

Botanical classification: *Agave bracteosa* (Zucc.).
Variety denomination: 'Stingray'.

BACKGROUND OF THE INVENTION

The present invention relates to the new and distinct Variegated squid *Agave* plant, *Agave* 'Stingray' selected by Hans A. Hansen at a perennial nursery in Raleigh, N.C., USA as an uninduced whole-plant mutation from a tissue cultured crop of *Agave bracteosa* 'Calamar' (not patented) in the summer of 2009. The new plant has been successfully asexually propagated by division and shoot tip tissue culture at a nursery in Zeeland, Mich. Shoot tip tissue culture propagation systems have been found produce stable and identical plants that maintain the unique characteristics of the original plant.

No plants of *Agave* 'Stingray' have been sold, in this country or anywhere in the world, prior to the filing of this application, nor has any disclosure of the new plant been made prior to the filing of this application with the except that which was disclosed within one year of the filing of this application and was either derived directly or indirectly from the inventor.

BRIEF SUMMARY OF THE INVENTION

*Agave* 'Stingray' differs from its parent, 'Calamar', as well as all other *Agaves* known to the applicant. 'Calamar' is a solid green form of *Agave bracteosa*. The most similar known *Agave* cultivars other than the parent are: 'Monterrey Frost' (not patented), 'Summer Snow' (not patented) and 'Daddy Longlegs' (not patented). 'Monterrey Frost' has a more white margin, 'Summer Snow' has wider whiter margin, and 'Daddy Longlegs' has a subtle chartreuse margin, rather than the creamy yellow margins of 'Stingray'. 'Campostella' (not patented) has variegated leaves with a yellow center and green margin. 'Squiddo' (not patented) has variegated leaves with a creamy yellow center and green margin. 'Moroccan Princess' (not patented) has variegated leaves with white center and green margins.

*Agave* 'Stingray' differs from all other *Agaves* known to the applicant, by the combination of the following traits:

1. Long, arching, linear foliage without lateral spines or sharp apical spines;
2. Leaves have creamy yellow margins and contrasting medium green leaf centers.
3. Habit is upright near base and arching to drooping distally.

BRIEF DESCRIPTION OF THE DRAWINGS

The photograph of the new plant demonstrates the overall appearance of the new plant including the unique traits as a five-year old plant grown in a container in a greenhouse with supplemental water and fertilizer as needed. The colors are as accurate as reasonably possible with color reproductions. Ambient light spectrum, temperature, source and direction may cause the appearance of minor variation in color.

DETAILED BOTANICAL DESCRIPTION

Figure 1:
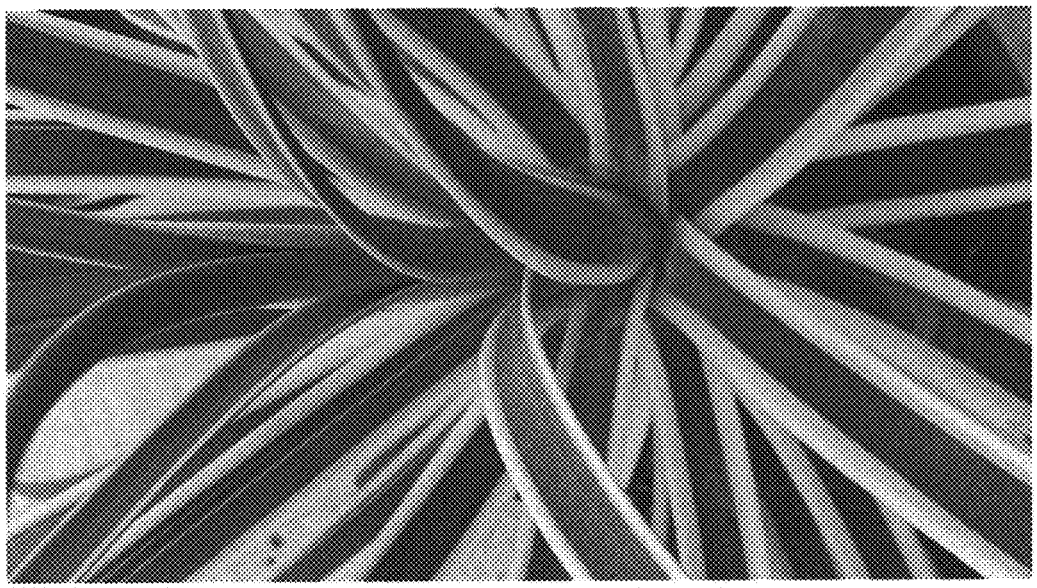
FIG. 1 shows a close-up of the new plant in a container with new foliage in the center.
Figure 2:
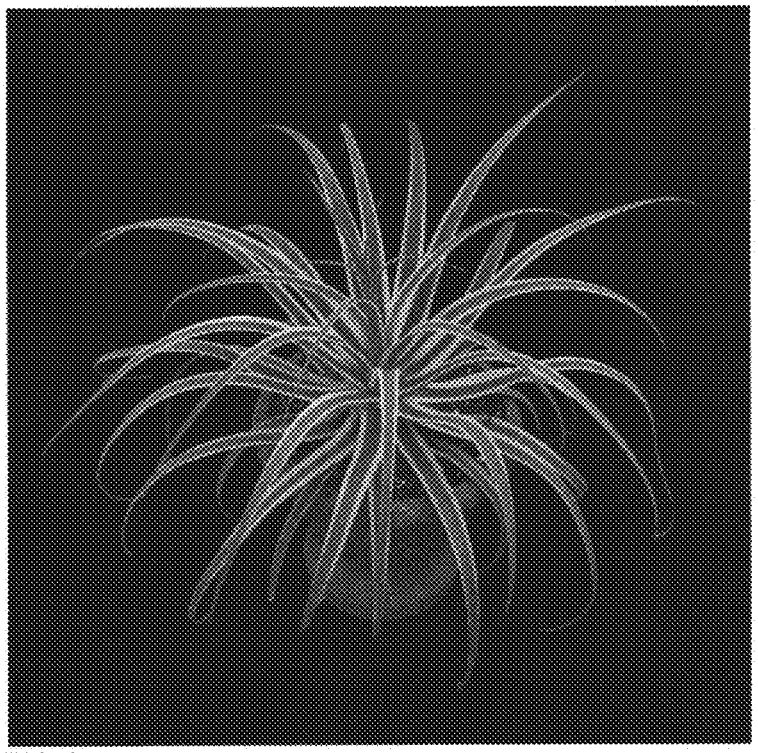
FIG. 2 shows the habit of the foliage of the whole plant.

The following descriptions and color references are based on the 2015 edition of The Royal Horticultural Society Colour Chart except where common dictionary terms are used. The new plant, *Agave* 'Stingray', has not been observed under all possible environments. The phenotype may vary slightly with different environmental conditions, such as temperature, light, fertility, moisture and maturity levels, but without any change in the genotype. The following observations and size descriptions are of a five-year old plant in a commercial wholesale greenhouse in Zeeland, Mich. with supplemental water and fertilizer as needed.

Botanical classification: *Agave bracteosa* (S. Watson ex Englm.);
Variety denomination: 'Stingray';
Sport parentage: Uninduced whole-plant sport of *Agave* 'Calamar';
Propagation: Garden division and sterile plant tissue culture;
Time to initiate roots from tissue culture: About 21 days;
Growth rate: Moderate to slow;

Crop time: About 16 weeks to finish during the summer in a 3.8 liter container from an established 2.5 cm tissue culture plug;

Rooting habit: Fleshy, lightly branching, with roots up to 20 cm long;

Root color: Nearest RHS 158C;

Plant shape and habit: Herbaceous tender perennial with basal rosettes of long, narrow, whorled leaves emerging from central base, producing a symmetrical upright to arching rounded mound;

Plant size: Foliage height about 56.0 cm tall from soil line to the top of the leaves and about 90.0 cm wide at the widest point about 40.0 cm above soil line;

Foliage description: Linear, simple, fleshy; margins micro-serrate; narrowly acute apex ending in long flexible spine; truncate to flared sessile base; glabrous and slightly glaucous abaxial and adaxial; upright proximally becoming arching and drooping toward apex;

Number of leaves: About 84 per plant;

Leaf size: To about 60.0 cm long, 5.3 cm wide at flared base, 3.5 cm wide in middle and 12.0 mm thick at base; average 56.0 cm long, 5.0 cm wide at flared base, 3.4 cm wide in middle and 12.0 thick at base;

Leaf variegation size: Adaxial margin to 18 mm wide at base, about 4.0 mm in longitudinal middle and tapering to about 1.0 mm at apex; abaxial margin to about 17.0 mm wide at base, 4.0 mm wide in longitudinal middle and tapering to about 1.0 mm at apex; intermediate zone between creamy yellow margins and medium green center widest in longitudinal center and not noticeable at abaxial or adaxial base or apex, to about 5.0 mm wide in adaxial longitudinal center and 3.0 mm wide in abaxial longitudinal center;

Foliage fragrance: None observed;

Stem: To about 6.5 cm wide and about 6.5 cm tall; covered with leaves;

Leaf blade color:

*Mature adaxial apex*.—Margin between RHS 144A and RHS 146D, center nearest RHS 137B; base: margin nearest RHS 11B, center blend between RHS 137C and RHS 146A.

*Mature abaxial apex*.—Margin nearest RHS 146D and center nearest RHS 146C.

*Mature adaxial base*.—Margin nearest RHS 11B and center blend between RHS 137C and RHS 146B.

*Mature abaxial base*.—Margin nearest RHS 11B and center between RHS 144C and RHS 144D.

*Mature adaxial longitudinal center*.—Margin nearest RHS 5D, center blend between RHS 137C and RHS 146A, intermediate zone nearest RHS 11B with undertone nearest RHS 138B.

*Mature abaxial longitudinal center*.—Margin nearest RHS 8D, center blend between RHS 137C and RHS 146C, intermediate zone nearest RHS 8C with undertone nearest RHS 138B.

*Expanding young adaxial and abaxial margin nearest RHS* 145D and adaxial and abaxial center nearest RHS 144A.

Spine: Apical spine to about 14.0 mm long, flexible, even when dried; color nearest RHS 199A;

Marginal spines: Micro-serrate; color nearest RHS 5D;

Petiole: Sessile;

Veins: Absent;

Flower description: Flowers have not yet been observed;

Fruit and seed: Have not yet been observed;

Disease resistance: *Agave* 'Stingray' has not been observed to be resistant to diseases common to *Agaves* beyond that which is normal for *Agave*. The plant is xeromorphic and survives well with minimal water once established. Hardiness at least from USDA zone 8 to 10. Extent of winter hardiness has not been tested.

I claim:

1. A new and distinct cultivar of ornamental *Agave* plant named 'Stingray' as herein described and illustrated.

* * * * *